(12) United States Patent
Salmons et al.

(10) Patent No.: US 10,329,526 B2
(45) Date of Patent: Jun. 25, 2019

(54) METHOD OF FREEZE-DRYING ENCAPSULATED CELLS, FREEZE-DRIED ENCAPSULATED CELLS, COMPOSITIONS CONTAINING FREEZE-DRIED ENCAPSULATED CELLS AND USES OF SUCH CELLS AND COMPOSITIONS

(71) Applicant: AUSTRIANOVA SINGAPORE PTE LTD., Singapore (SG)

(72) Inventors: Brian Salmons, Singapore (SG); John A. Dangerfield, Singapore (SG); Walter H. Guenzburg, Singapore (SG)

(73) Assignee: Austrianova Singapore Pte Ltd., Singapore (SG)

( * ) Notice: Subject to any disclaimer, the term of this patent is extended or adjusted under 35 U.S.C. 154(b) by 0 days.

(21) Appl. No.: 14/902,539

(22) PCT Filed: Jul. 2, 2014

(86) PCT No.: PCT/EP2014/064087
§ 371 (c)(1),
(2) Date: Dec. 31, 2015

(87) PCT Pub. No.: WO2015/000972
PCT Pub. Date: Jan. 8, 2015

(65) Prior Publication Data
US 2016/0298077 A1    Oct. 13, 2016

(30) Foreign Application Priority Data
Jul. 2, 2013   (EP) .................................... 13174681

(51) Int. Cl.
| | |
|---|---|
| C12N 1/04 | (2006.01) |
| A01N 1/02 | (2006.01) |
| C12N 1/20 | (2006.01) |
| C12N 11/04 | (2006.01) |
| C12N 11/10 | (2006.01) |
| C12N 11/12 | (2006.01) |
| A61K 35/747 | (2015.01) |
| A23L 33/135 | (2016.01) |
| A61K 9/19 | (2006.01) |
| A61K 9/48 | (2006.01) |
| A61K 9/50 | (2006.01) |
| A61K 35/745 | (2015.01) |
| A61K 35/00 | (2006.01) |

(52) U.S. Cl.
CPC ............. *C12N 1/04* (2013.01); *A01N 1/0221* (2013.01); *A01N 1/0231* (2013.01); *A23L 33/135* (2016.08); *A61K 9/19* (2013.01); *A61K 9/4858* (2013.01); *A61K 9/4875* (2013.01); *A61K 9/5042* (2013.01); *A61K 35/745* (2013.01); *A61K 35/747* (2013.01); *C12N 1/20* (2013.01); *C12N 11/04* (2013.01); *C12N 11/10* (2013.01); *C12N 11/12* (2013.01); *A23V 2002/00* (2013.01); *A23Y 2220/03* (2013.01); *A23Y 2220/17* (2013.01); *A23Y 2300/45* (2013.01); *A61K 2035/115* (2013.01)

(58) Field of Classification Search
None
See application file for complete search history.

(56) References Cited

U.S. PATENT DOCUMENTS

| | | | | |
|---|---|---|---|---|
| 5,071,741 A | * | 12/1991 | Brockbank | .............. A01N 1/02 128/898 |
| 5,518,878 A | * | 5/1996 | Wilkins | ............... A01N 1/0221 435/1.3 |
| 5,691,133 A | * | 11/1997 | Critser | ................. A01N 1/0263 435/1.3 |
| 8,968,721 B2 | | 3/2015 | Harel | |
| 2006/0246414 A1 | * | 11/2006 | Chang | ................. A01N 1/0221 435/2 |
| 2010/0311036 A1 | | 12/2010 | He | |

FOREIGN PATENT DOCUMENTS

| | | | | |
|---|---|---|---|---|
| EP | 0800765 | * | 10/1997 | ............... A01N 1/02 |
| EP | 2789340 A1 | | 10/2014 | |
| JP | H09505032 A | | 5/1997 | |
| JP | 2002000248 A | | 1/2002 | |
| JP | 2012508584 A | | 4/2012 | |
| JP | 2012525338 A | | 10/2012 | |

(Continued)

OTHER PUBLICATIONS

Zhang et al., J. Zhejiang Univ-Sci. B (Biomed. Biotechnol.)11(11):889-894 (2010).*
Zhao et al., J. App. Microbiol., 99:333-338 (2005).*
Hubalek et al., Cryobiol., 46:205-229 (2003).*
Soukoulis et al., Food Bioprocess Technol., 7:1255-1268 (2014).*
Chan et al., Carb. Poly., 83:225-232 (2011).*
Guan et al., Cryobiol., 65:179-187 (2012).*
Mukherjee et al., Cryobiol., 55(1):10-18 (2007).*
Hunt et al., Transfus. Med. Hemother, 38:107-123 (2011).*
Jalali et al., Res. Pharm. Sci., 7(1):31-36 (2012).*
Huang et al. "Optimization of a protective medium for enhancing the viability of freeze-dried *Lactobacillus delbrueckii* subsp. *bulgaricus* based on response surface methodology", J Ind Microbiol Biotechnol. Jan. 2006;33(1):55-61. Epub Oct. 22, 2005. (Abstract Only).

(Continued)

*Primary Examiner* — Thomas J. Visone
(74) *Attorney, Agent, or Firm* — Acuity Law Group, PC; Michael A. Whittaker

(57) ABSTRACT

The disclosure provides a method of freeze-drying encapsulated cells, the method comprising at least two consecutive incubation steps, wherein the encapsulated cells are incubated in each incubation step in an incubation solution containing cryoprotectant over a suitable period of time, wherein the concentration of cryoprotectant in the incubation solution is increased with each subsequent incubation step. The disclosure also provides freeze dried cells that are obtained by this method as well as various uses of these cells as pharmaceutical, food additive or additive in cosmetics. The disclosure also provides a composition that contains skim milk, glycerol and a carbohydrate.

8 Claims, 9 Drawing Sheets

(56) References Cited

FOREIGN PATENT DOCUMENTS

| WO | 9507611 A1 | 3/1995 |
|---|---|---|
| WO | 2010057039 A2 | 5/2010 |
| WO | 2010124387 A1 | 11/2010 |
| WO | 2012101167 A1 | 2/2012 |

OTHER PUBLICATIONS

Office Action issued in European Patent Application No. 14744005.1 dated Apr. 13, 2017—3 pages total.
Capela et al., Effect of cryoprotectants, prebiotics and microencapsulation on survival of probiotic organisms in yoghurt and freeze-dried yoghurt. Food Research International Mar. 2006;39(2):203-211.
De Angelis and Gobbetti, Environmental stress responses in Lactobacillus: A review. Proteomics. Jan. 2004;4(1):106-122.
Franks, Protein destabilization at low temperatures. Adv Protein Chem. 1995;46:105-139.
Gordon et al., Recovery of Human Mesenchymal Stem Cells Following Dehydration and Rehydration. Cryobiology. Sep. 2001;43(2):182-187.
Islam et al., Microencapsulation of Live Probiotic Bacteria. J Microbiol Biotechnol. Oct. 2010;20(10):1367-1377.
Kanmani et al., Cryopreservation and Microencapsulation of a Probiotic in Alginate-chitosan Capsules Improves Survival in Simulated Gastrointestinal Conditions. Biotechnology and Bioprocess Engineering 2011;(16):1106-1114.
Santivarangkna et al., Alternative Drying Processes for the Industrial Preservation of Lactic Acid Starter Cultures. Biotechnol Prog. Mar.-Apr. 2007;23(2):302-315.
Thammavongs et al., Physiological response of Enterococcus faecalis JH2-2 to cold shock: Growth at low temperatures and freezing/thawing challenge. Lett Appl Microbiol. Dec. 1996;23(6):398-402.
Wikstrom et al., Viability of freeze dried microencapsulated human retinal pigment epithelial cells. Eur J Pharm Sci. Sep. 29, 2012;47(2):520-526.
Ayama et al., "Effect of encapsulation of selected probiotic cell on survival in simulated gastrointestinal tract condition", Songklanakarin J. Sci. Technol., 36 (3), 291-299, May-Jun. 2014.
Office Action issued in Japanese Patent Application No. 2016-522603 dated May 8, 2018 (8 pages total)—incl Engl lang transl.

\* cited by examiner

METHOD OF FREEZE-DRYING ENCAPSULATED CELLS, FREEZE-DRIED ENCAPSULATED CELLS, COMPOSITIONS CONTAINING FREEZE-DRIED ENCAPSULATED CELLS AND USES OF SUCH CELLS AND COMPOSITIONS

CROSS-REFERENCE TO RELATED APPLICATIONS

The present invention is filed under 35 U.S.C. § 371 as the U.S. national phase of International Application No. PCT/EP2014/064087, filed 2 Jul. 2014, which designated the U.S. and claims the right of priority of European patent application no. 13 174 681.0 filed with the European Patent Office on 2 Jul. 2013, the entire contents of which are incorporated herein for all purposes.

FIELD OF THE INVENTION

The present invention relates generally to a method of freeze-drying encapsulated cells. The present invention also provides freeze dried cells that are obtained by this method as well as compositions containing the freeze dried encapsulated cells and various uses of these cells, for example, as pharmaceutical, as nutraceutical, as food additive or as additive in cosmetics. The invention also provides a new composition that contains skim milk, glycerol and a carbohydrate and that can for example be used for the freeze-drying of cells.

BACKGROUND OF THE DISCLOSURE

Probiotics are live microorganisms which, according to the World Health Organization (WHO) when administered in adequate amounts, confer a health benefit on the host. Particularly, *lactobacillus acidophilus* bacteria promote intestinal health which is a major aspect of the host's general well-being. Probiotic products require some process steps that ensure their stability and viability. They can be negatively influenced by storage and during their passage through the gastrointestinal tract upon consumption.

Many probiotic products are freeze-dried to preserve them until they are used. This means they are first deep-frozen and afterwards dehydrated in a vacuum. The freeze-drying process is crucial for maintaining the stability and viability of probiotic bacteria as food additive, food supplement or nutraceutical.

Technically, freeze-drying, also known as lyophilization, lyophilization, or cryodesiccation, can be defined as cooling of liquid sample, resulting in the conversion of freeze-able solution into ice, crystallization of crystallisable solutes and the formation of an amorphous matrix comprising non-crystallizing solutes associated with unfrozen mixture, followed by evaporation (sublimation) of water from amorphous matrix. The evaporation (sublimation) of the frozen water in the material is usually carried out by reducing the surrounding pressure to allow the frozen water in the material to sublimate directly from the solid phase to the gas phase. The great advantage of freeze drying is to stabilize the materials for storage.

Furthermore, freeze-drying has the advantage of no risk of thawing to the encapsulated cells (Santivarangkna, C., Kulozik, U. and Foerst, P. (2007) Alternative drying processes for the industrial preservation of lactic acid starter cultures. Biotechnology Progress, 23(2), 302-315). Significant mortality of bacterial cells has been reported after freeze drying due to the loss of membrane integrity and denaturation of macromolecules. See Franks, F. (1995) "Protein destabilization at low temperatures". Advances in Protein Chemistry, 46, 105-139; Thammavongs, et al (1996) "Physiological response of *Enterococcus faecalis* JH2-2 to cold shock: Growth at low temperatures and freezing/thawing challenge" Letter in Applied Microbiology, 23(6), 398-402; De Angelis, M. and Gobbetti, M. (2004) "Environmental stress responses in *Lactobacillus*: A review" Proteomics, 4(1), 106-122.

It has been shown that encapsulation of bacteria in cellulose sulphate is able to exert a protecting effect on bacteria during freeze-drying. One study conducted with alginate-chitosan as encapsulation material mentioned that the capsules became swollen when they are incubated in simulated intestinal fluid (Paulraj Kanmani, R. Satish Kumar, N. Yuvaraj, K. A. Paari, V. Pattukumar, and Venkatesan Arul (2011) Cryopreservation and Microencapsulation of a Probiotic in Alginate-chitosan Capsules Improves Survival in Simulated Gastrointestinal Conditions. Biotechnology and Bioprecess Engineering, (16) 1106-1114. Kanmani et al. also describe in this study that sodium alginate-chitosan coated microcapsules shrank by 10% when in contact with simulated gastric fluid.

Thus, the detrimental action of the freeze drying process on cells such that bacterial cells might be offset by microencapsulation with sodium cellulose sulphate since such an encapsulation material may result in an improved stability of capsules and higher viability of encapsulated bacteria. However, there is still a need to overcome the detrimental action of the freeze drying process on cells such as bacterial cells.

SUMMARY OF THE INVENTION

The present invention addresses this need by providing new methods for freeze-drying encapsulated cells, encapsulated cells obtained by such methods and various uses of these encapsulated cells and compositions containing these encapsulated cells.

In a first aspect, the disclosure provides a method of freeze-drying encapsulated cells, the method comprising at least two consecutive incubation steps, wherein the encapsulated cells are incubated in each incubation step in an incubation solution containing cryoprotectant over a suitable period of time, wherein the concentration of cryoprotectant in the incubation solution is increased with each subsequent incubation step.

In a second aspect, the disclosure provides a freeze-dried encapsulated cell that is obtained by a method of freeze-drying encapsulated cells as described here.

In a third aspect, the disclosure provides a composition comprising a suitable carrier and an encapsulated cell that is obtained by a method of freeze-drying encapsulated cells as described here. In exemplary embodiments the composition can, for example, be a food supplement for humans or animals, a soap formulation, a cosmetic composition or a pharmaceutical composition.

In a fourth aspect the disclosure provides a method of treating or preventing of diarrhoea, antibiotic caused diarrhoea, arthritis, obesity, irritable bowel syndrome, heartburn, chronic fatigue syndrome, gastrointestinal cancer and other forms of suffering from an unbalanced bacterial population in the intestine, the method comprising administering to a subject a freeze-dried encapsulated cell or a composition containing a freeze-dried encapsulated cell as disclosed herein.

In a fifth aspect, the disclosure provides the use of a freeze-dried encapsulated cell or a composition containing freeze-dried encapsulated as disclosed herein for treating or preventing of diarrhoea, antibiotic caused diarrhoea, arthritis, obesity, irritable bowel syndrome, heartburn, chronic fatigue syndrome, gastrointestinal cancer and other forms of suffering from an unbalanced bacterial population in the intestine.

In a sixth aspect, the disclosure provides for the use of a freeze-dried encapsulated cell or a composition containing a freeze-dried encapsulated cell as disclosed herein as a pharmaceutical, a food additive or an additive in cosmetics. In exemplary embodiments of the invention, when used as food additive, the food can be a milk-based product such as yoghurt, cottage cheese, or butter milk. In other exemplary embodiments of the invention, when used as food additive, a freeze-dried encapsulated cell or the composition containing a freeze-dried encapsulated cell as disclosed herein as is stored in a separate compartment of a food package containing the food.

In a seventh aspect the disclosure provides a method of preparing encapsulated cells for freeze-drying, the method comprising at least two consecutive incubation steps, wherein the encapsulated cells are incubated in each incubation step in an incubation solution containing cryoprotectant over a suitable period of time, wherein the concentration of cryoprotectant in the incubation solution is increased with each subsequent incubation step.

In an eight aspect, the disclosure provides for a freeze-dried encapsulated cell prokaryotic cell or a freeze-dried encapsulated yeast cell.

In an ninth aspect, the disclosure provides for a composition that is suitable for freezing of cells, the composition comprising skim milk, glycerol and a carbohydrate.

In a tenth aspect, the disclosure provides for a method of preparing encapsulated cells for freeze-drying, the method comprising incubating the encapsulated cells in a composition comprising skim milk, glycerol and a carbohydrate.

In an eleventh aspect, the disclosure provides for the use of a composition comprising skim milk, glycerol and a carbohydrate for preparing encapsulated cells for freeze-drying.

In a twelfth aspect, the disclosure provides for the use of a composition comprising skim milk, glycerol and a carbohydrate for the freezing of encapsulated cells.

DESCRIPTION OF THE DRAWINGS

The invention will be better understood with reference to the detailed description when considered in conjunction with the non-limiting examples and the accompanying drawings, in which.

DETAILED DESCRIPTION

Figure 1:
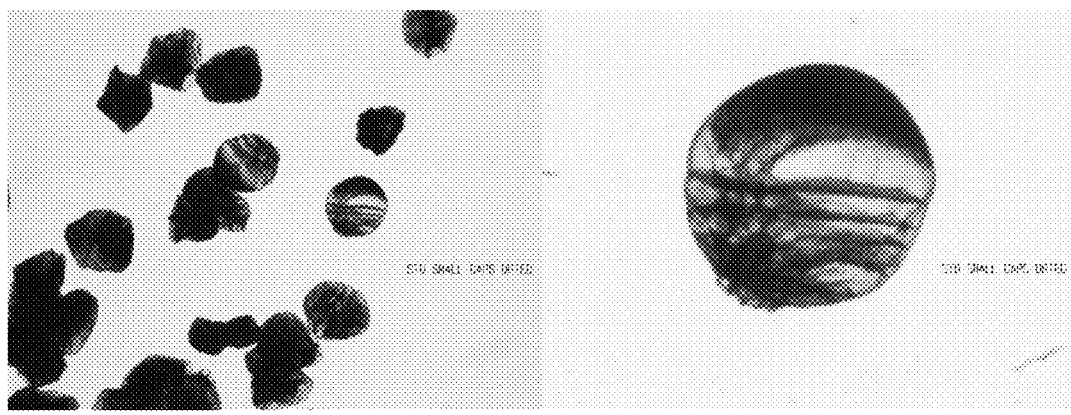
FIG. 1 shows bright field microscopic images of encapsulated *Lactobacillus acidophilus* cells in freeze dried form after being treated with the method of the invention using 5% skimmed milk powder and 1% glycerol as cryoprotectant, wherein in the cells were incubated in each incubation step in an incubation solution containing increasing concentration of the cryoprotectant. The increasing concentrations of the cryoprotectant are achieved by serially diluting in each incubation step the bacterial growth solution from 100% to 50% to 25% to 12.5% to 6.25% to 3.125% to 0% with cyroprotectant solution (5% skimmed milk powder and 1% glycerol)

The present invention provides a method of freeze-drying encapsulated cells, wherein this method comprises at least two consecutive incubation steps. The encapsulated cells are incubated in each of the incubation steps in an incubation solution containing cryoprotectant over a suitable period of time, wherein the concentration of cryoprotectant in the incubation solution is increased with each subsequent incubation step. The inventors have found this method provides a protective effect on the (structural) integrity of capsules (the encapsulation material) both before and during the freeze-drying process. In addition, the shelf-life of the capsules with the cells encapsulated therein is extended and the viability of the encapsulated cells is significantly increased (cf. Example Section). On a mechanistic level, while not wishing to be bound by theory, it is believed that subjecting the encapsulated cells to the at least two consecutive incubation steps of the method of the invention avoids capsules from "crumpling".

The increase of the concentration of the cryoprotectant (it is noted here that the term "cryoprotectant" as used herein refers to both a single cryoproctant and a mixture/combination of two or more cryoprotectants) in the incubation solution during the consecutive incubation steps can be achieved in various ways. It is, for example, possible, to add to a suspension of the encapsulated cells, for each incubation step a stock solution of the cryo-protectant. For example, if a cryoprotectant such as DMSO, formamide, N-methylacetamide (MA), or propanediol is used, a stock solution of the pure cryoprotectant (100% stock solution) might be used and in each incubation step a certain amount of the stock solution is added to the cell suspension to increase the concentration of the cryoprotectant (cf. Example 1 of the Example Section). Alternatively, it is, for example, also possible to use the solution in which the encapsulated cells will be subjected to the freeze-drying (i.e., the freezing solution or cryopreservation medium) as a starting/stock solution to achieve an increasing in the concentration of the cryoprotectant. Using the final freezing solution for this purpose has the advantage that no extra stock solution has to be prepared for the consecutive incubation steps. This approach simplifies the handling of the incubation steps when a mixture of cryoprotectants are used in the incubation steps, say, for example, a mixture of skim milk powder with glycerol or a mixture of skim milk powder, glycerol and a carbohydrate such as sucrose or trehalose. In such a case, the prepared freezing solution (say, for example, 5% (w/v) skim milk and 1% (v/v) glycerol in water or an aqueous solution of 5% (w/v) skim milk, 1% (v/v) glycerol and 10% (w/v) of a carbohydrate such as sucrose or trehalose), is used to "serially dilute" in each incubation step the medium in which the encapsulated cells are stored. This "serial dilution" can, for example, be achieved as follows. Half the volume of the cell medium in which the encapsulated cells are present is removed from the respective vial, and the same volume of the freezing solution is added for the first incubation step. The encapsulated cells are then incubated for the desired period of time and then again 50% of the volume of the incubation mixture is removed and replaced by the same volume of freezing solution for the second incubation step. This procedure can be repeated as often as desired, thereby increasing the concentration of the cryoprotectant in each incubation step. If wanted the last incubation step may be carried out in the freezing solution.

The term "freeze-drying" which is also known as lyophilisation, lyophilization, or cryodesiccation, is used in its regular meaning as the cooling of a liquid sample, resulting in the conversion of freeze-able solution into ice, crystallization of crystallisable solutes and the formation of an amorphous matrix comprising non-crystallizing solutes associated with unfrozen mixture, followed by evaporation (sublimation) of water from amorphous matrix. In this process the evaporation (sublimation) of the frozen water in the material is usually carried out under reducing the surrounding pressure to allow the frozen water in the material to sublimate directly from the solid phase to the gas phase. Freeze-drying typically includes the steps of pretreatment, freezing, primary drying and secondary drying.

The pretreatment includes any method of treating the desired product, i.e. here encapsulated cells, prior to freezing. The pretreatment may, for example, include washing the cells, formulation revision (i.e., addition of components to increase stability and/or improve processing), or decreasing the amount of a high vapor pressure solvent or increasing the surface area.

The freezing step includes any method that is suitable for freezing of the encapsulated cells. On a small scale, for example, in a laboratory, freezing may be done by placing the material in a freeze-drying flask and rotating the flask in a bath, also known as a shell freezer, which is cooled by, for example, mechanical refrigeration, by a mixture of dry ice with an alcohol such as methanol or ethanol, or by liquid nitrogen. It is of course also possible to use a commercially available freeze-dry apparatus such as Thermo Scientific® Modulyo Freeze-Dry System distributed by Thermo Fisher Scientific Inc. On a larger scale, freezing is generally using a commercial, temperature controlled freeze-drying machine. When freezing the encapsulated cells, the freezing is generally carried out rapidly, in order to avoid the formation of ice crystals. Usually, the freezing temperatures are between −50° C. and −80° C.

The next step is the primary drying. During the primary drying phase, the pressure is lowered (typically to the range of a few millibars), and sufficient heat is supplied to the material for the water to sublime. The amount of heat necessary can be calculated using the sublimating molecules' latent heat of sublimation. In this initial drying phase, about 95% of the water in the material is sublimated. This phase may be slow (can be several days in the industry), because, if too much heat is added, the material's structure could be altered.

Secondary drying can follow as the last step in freeze drying. The secondary drying phase aims to remove, if present, unfrozen water molecules, since the ice was removed in the primary drying phase. In this phase, the temperature is usually higher than in the primary drying phase, and can even be above 0° C., to break any physicochemical interactions that have formed between the water molecules and the frozen material. Usually the pressure is also lowered in this stage to encourage desorption (typically in the range of microbars, or fractions of a pascal). After the freeze-drying process is complete, the vacuum is usually broken with an inert gas, such as nitrogen, before the freeze-dried encapsulated cells are packaged and/or stored for the further use.

As evident from the above, the present method belongs to the "pretreatment" as understood by the person skilled in the art and can be used together with any known methodology of freezing and drying material such as free or encapsulated cells as described herein.

Accordingly, since the at least two consecutive incubation steps can be carried out with any suitable following freeze-drying steps, the invention is also directed to a method of preparing encapsulated cells for freeze-drying, wherein this method comprises at least two consecutive incubation steps, wherein the encapsulated cells are incubated in each incubation step in an incubation solution containing cryoprotectant over a suitable period of time, wherein the concentration of cryoprotectant in the incubation solution is increased with each subsequent incubation step. Thus, while in the following the invention will be explained in more detail with reference to a freeze-drying method, it should be understood that all these embodiments equally relate to the method of preparing encapsulated cells for freeze-drying as defined here.

In the method of the invention any suitable number of the least two consecutive incubation steps can be carried as long as the number is sufficient to provide a desired effect on, for example, the viability of the encapsulated cells after the freeze-drying. In illustrative embodiments the method comprises 3, 4, 5, 6, 7, 8, 9 or 10 incubation steps, wherein in each incubation step the concentration of the cryoprotectant is increased. The incubation in each of the incubation steps can be carried out over any suitable amount of time, for example, a time that is found to be able to achieve a desired long-term stability of the capsules and/or the viability of the encapsulated cells. A suitable incubation time as well as a suitable the number of incubation steps can be determined empirically, for example, by assessing the viability of the encapsulated cells after freeze-drying followed by (after a certain time period) re-hydrating of the cells (cf. the Example Section in this regard). In some embodiments the incubation time is typically about several minutes to about several hours per incubation step (cf., also in this regard the Example Section in which bacterial cells were incubated in each incubation step for about 25 minutes). The incubation can be carried out either without agitation but also under agitation (such as, for instance, shaking or rolling) to improve the uptake of the cryoprotectant by the encapsulation material and the cells.

In some embodiments of the method of the invention, the same cryoprotectant or a mixture of the same cryoprotectant is used in each incubation step. The cryoprotectant can be any compound that is able to provide protection during the freeze-drying against damage to the use encapsulation material or the encapsulated cell. Examples of suitable cryoprotectants include, but are not limited to, skim milk, glycerol, dimethylsulfoxide (DMSO), formamide, a mixture of formamide and DMSO, N-methylacetamide (MA), polyvinylpyrrolidone, propanediol (either 1,2-propanediol or 1,3-propanediol or a mixture of both), propylene glycol, serum albumin, a mixture of serum albumin with methanol, a carbohydrate and alginate. Examples of alginates that can be used as cryoprotectant include Satialgine® alginate or Algogel® alginate that are both available from Cargill (cf. P. Capelaa et al, "Effect of cryoprotectants, prebiotics and microencapsulation on survival of probiotic organisms in yoghurt and freeze-dried yoghurt" Food Research International Volume 39, Issue 2, March 2006, Pages 203-211)

Examples of carbohydrates that can be used as cryoprotectant include, but are not limited to sucrose, glucose mixed with methanol, lactose, trehalose, raffinose, dextran, pectin (for example, Unipectine™ that is also available from Cargill and that has been also by discussed as cryoprotectant by P. Capelaa et al, Food Research International Volume 39, supra), hydroxyethyl starch (HES), and cellulose sulphate.

It is also possible to use in the present invention a mixture of two or more cryoprotectants in the incubation solution, for example, but by no means limited to, a mixture of skim milk with glycerol or a mixture of skim milk with a carbohydrate (cf. the Example Section). In such embodiments, it is possible that the concentration of only one of the cryoprotectants is increased in the consecutive incubation steps while the concentration of the second (or any further) cryoprotectant is held constant during the course of the incubation (see also the Example Section). In one of such embodiments, the cryoprotectant the concentration of which is held constant may be chosen from sucrose, glucose mixed with methanol, lactose, trehalose, raffinose, or dextran. In one particular embodiment, the concentration of skim milk is increased in each of the at least two consecutive incubation steps while the concentration of the carbohydrate (for example, sucrose, glucose mixed with methanol, lactose, trehalose, raffinose, or dextran) is held constant in the at least two consecutive incubation steps.

Any suitable (encapsulated) cell can be used in the present invention. The encapsulated cell may be a eukaryotic cell or a prokaryotic cell or a mixture of several eukaryotic cells or several prokaryotic cells. The cells can also be a mixture of eukaryotic cells with prokaryotic cells. Examples of eukaryotic cells include, but are not limited to, mammalian cells, fungal cells or yeast cells. A purely illustrative example for mammalian cells are the human retinal pigment epithelial (RPE) cells described by Wikström et al. "Viability of freeze dried microencapsulated human retinal pigment epithelial cells" Eur. J. Pharm. Sci. Volume 47, Issue 2, 29 Sep. 2012, Pages 520-526 or the mesenchymal stem cells described by Gordon et al, 2001, "Recovery of human mesenchymal stem cells following dehydration and rehydration" Cryobiology 43, 182. Examples of suitable yeast cells include *Saccharomyces, Debaromyces, Candida, Pichia* and *Torulopsis*, to mention only a few illustrative examples. Examples of fungal cells include, but are of course not limited to, *Aspergillus, Rhizopus, Mucor or Penicillium*. The prokaryotic cells used in the present invention can be bacterial cells. The bacterial cells can be aerobic or anaerobic cells. In illustrative examples of the method of the invention, the bacterial cells may be selected from the group consisting of *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus, Geobacillus, Lactobacillus* and mixture of these cells.

In some embodiments of the present method, the cells that are subjected to the incubation as disclosed herein are probiotic cells. Examples of suitable probiotic cells include, but are not limited to *Saccharomyces cereviseae, Bacillus coagulans, Bacillus licheniformis, Bacillus subtilis, Bifidobacterium angulatum, Bifidobacterium animalis, Bifidobac-* terium bifidum, Bifidobacterium breve, Bifidobacterium infantis, Bifidobacterium lactis, Bifidobacterium longum, Enterococcus faecium, Enterococcus faecalis, Lactobacillus acidophilus, Lactobacillus amylovorus, Lactobacillus alimentarius, Lactobacillus bulgaricus, Lactobacillus casei subsp. casei, Lactobacillus casei Shirota, Lactobacillus curvatus, Lactobacillus delbrueckii subsp. lactis, Lactobacillus fermentum, Lactobacillus farciminus, Lactobacillus gasseri, Lactobacillus helveticus, Lactobacillus johnsonii, Lactobacillus lacti, Lactobacillus paracasei, Lactobacillus pentosaceus, Lactobacillus plantarum, Lactobacillus reuteri, Lactobacillus rhamnosus (Lactobacillus GG), Lactobacillus sake, Lactobacillus salivarius, Lactobacillus thermotolerans, Lactobacillus mucosae, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus, Staphylococcus xylosus and any mixture of these cells.

In some embodiments of the invention, in particular, when bacterial cells or eukaryotic cells such as yeasts are employed, the cells are in an exponential growth phase when being encapsulated. It is however of course also possible to encapsulate and subsequently freeze-dry cells that are in any other growth phase, for example, mammalian cells that are grown to confluence (cf in this respect Wikström et al, Eur. J. Pharm. Sci. (2012) supra).

In typical embodiments of the invention, the cells have been encapsulated in a microcapsule having a porous capsule wall. The porous capsule wall (shell) may comprise a material selected from the group consisting of an alginate polymer, collagen, gelatine, chitosan, agarose, a poly-lysine polymer, a cellulose sulphate polymer and combinations thereof.

In this context, it is noted that the term "encapsulation" is used in the present invention in accordance with its conventional meaning within the art. Encapsulation as used herein refers to the process of forming a continuous coating around an inner matrix or cell that is wholly contained within the capsule wall as a core of encapsulated material. Encapsulation is to be distinguished from "immobilisation" which refers to the trapping of material such as cells within or throughout a matrix. In contrast to encapsulation, immobilisation is a random process resulting in undefined particle size where a percentage of immobilised elements will be exposed at the surface. Encapsulation or microencapsulation (both terms are used herein interchangeably) helps to separate a core material from its environment, thereby improving its stability and extending the shelf-life of the core material. The structure formed by the microencapsulation agent around the core substance is known as the wall or shell. The properties of the wall system are typically designed to protect the core material and to potentially release the core material under specific conditions while allowing small molecules to pass in and out of the porous capsule wall (that acts as a membrane). Any capsule and encapsulating material can be subjected to the freeze-drying method as described herein. The capsules may, for example, range from submicron to several millimeters in size and can be of different shapes.

In accordance with the above disclosure several food grade biopolymers such as alginate, starch, xanthan gum, guar gum, locust bean gum and carrageenan gum as well as whey proteins have been tested as microencapsulation materials to protect, for example, acid sensitive microbial cells with varying successes. For a recent review see Islam et al. "Microencapsulation of Live Probiotic Bacteria" J. Microbiol. Biotechnol. (2010), 20(10), 1367-1377. All of these encapsulation materials and also all these probiotic bacteria can be used in the present invention. An overview about all encapsulation material and, for example, microbial cells that can be used in the present invention is given in the International patent application WO 2012/101167 "Protection Of Microbial Cells From Acidic Degradation".

The alginate polymer, if used herein as desired encapsulating material for cells, might be pure alginate polymer, a modified alginate-starch polymer, alginate-inulin-xanthan gum, alginate and poly L-lysine polymer a chitosan/alginate polymer and a chitosan/xanthan polymer. Numerous examples of such alginate encapsulation materials are disclosed in Wikström et al, supra or the International patent application WO 2012/101167 and the references cited in this International application.

In other embodiments of the invention, the encapsulating material can be a cellulose sulphate polymer. This polymer can be any known cellulose sulphate polymer, including but not limited to, a cellulose sulphate polymer that comprises a complex formed from sodium cellulose sulphate (NaCS)/poly[diallyl(dimethyl)ammoniumchloride] (pDADMAC). Numerous examples of such alginate encapsulation materials are disclosed in the International patent application WO 2012/101167 and the references cited in this International application.

In embodiments of the present method of freeze-drying an encapsulated cell (or of the method of preparing an encapsulating cell for freeze-drying), the encapsulated cells are transferred, after the consecutive at least two incubation steps, into a suitable freeze drying medium without an intermediate washing step. By "washing step" is in particular meant a step in which the incubated cells are contacted with a washing buffer/medium that is devoid of the cryoprotectant.

In other embodiments the encapsulated cells such as bacterial cells are freeze-dried in the suitable freeze drying medium after the last incubation step. In these embodiments the freeze drying medium may also contain a cryoprotectant. In these embodiments the freeze drying medium contains the same cryoprotectant as the incubation solution.

Examples of suitable cryoprotectants that can be used in the freezing step (which can be carried out after the method of the present invention) include, but are not limited to, skim milk, glycerol, dimethylsulfoxide (DMSO), formamide, a mixture of formamide and DMSO, N-methylacetamide (MA), serum albumin, a mixture of serum albumin with methanol, polyvinylpyrrolidone, propanediol, propylene glycol, a carbohydrate and alginate, to again mention only a few illustrative examples.

Examples of suitable carbohydrate based cryoprotectants include, but are not limited to sucrose, glucose mixed with methanol, lactose, trehalose, raffinose, dextran, pectin, hydroxyethyl starch (HES) and cellulose sulphate.

In typical embodiments of this freezing step, the freeze drying medium is an aqueous solution that contains the one or more cryoprotectant which has been chosen for the freezing step.

In accordance with the above disclosure, the present invention is also directed to a freeze-dried encapsulated cell that is obtained by a method as disclosed here. Also encompassed in the invention is a composition that comprises an encapsulated cell as disclosed herein together with a suitable carrier. The carrier can be any conventional carrier that is, for example, used in pharmaceuticals, cosmetics or foods. In line with, a composition of the invention may be a food supplement, a cosmetic composition or a pharmaceutical composition.

Examples of cosmetic compositions in which an encapsulated cell of the invention can be included are topical compositions such as soaps (both liquid or solid), lotions, make-up, cremes, shower gels, bathing salts, or hair wash. Illustrative examples of such compositions include probiotic bacterial cells such as Lactobacillus, Bifidobacterium or Bacillus coagulans (for example the strain GanedenBC$^{30}$® (Bacillus coagulans GBI-30, 6086 of Ganeden Biotec, Cleveland, Ohio, USA. Such cosmetic composition can, for example, be used to improve skin hydration, elasticity, under eye puffiness or to reduce fine lines and wrinkles in humans.

If an encapsulated cell obtained in the invention or a composition containing such an encapsulated cell is used as a supplement for food, the food may for example, be a cereal or a milk-based product such as yoghurt, curd, pudding, cottage cheese, or butter milk. If used as an additive for food such as yoghurt or pudding, an encapsulated cell of the invention or a composition containing an encapsulated cell of the invention can be stored in a separate compartment of a food package that contains the food. For example, the separate compartment may be bendable to allow to empty its content, meaning encapsulated cells of the invention or a respective composition into the other compartment of the food packaging which is filled, for example, with yoghurt or pudding. Using such a separate compartment allows to add, for example, encapsulated probiotic cells to food only before its consumption.

In line with this disclosure, the invention is also directed to various pharmaceutical or nutraceutical uses. Such uses include, but are not limited to, treating or preventing of diarrhoea, diarrhoea caused by antibiotic, arthritis, obesity, irritable bowel syndrome, heartburn, chronic fatigue syndrome and other forms of suffering from an unbalanced bacterial population in the intestine. For such uses, encapsulated cells of the invention or a composition containing such encapsulated cells are administered to a subject, usually a mammal such as human or a domestic animal or a farm animal such as cats, dogs, sheep, cows, pigs, poultry or fish, to name only few illustrative examples.

The invention is further directed to a composition that is suitable for freezing of cells, wherein the cells can either be encapsulated or free (not encapsulated) cells. Such a composition comprises skim milk, glycerol and a carbohydrate. Thus, this composition can be a freezing solution (or cryopreservation solution) that can be used in any freeze-drying methodology as described herein and as also known in the art. Such a composition thus comprises a carrier for the cryoprotectants (i.e. skim milk, glycerol and a carbohydrate). The carrier is typically (pure) water or an aqueous solution that contains salts, for example.

In embodiments of this composition the carbohydrate may be, but is not limited to sucrose, glucose mixed with methanol, lactose, trehalose, raffinose, dextran, pectin, hydroxyethyl starch (HES), cellulose sulphate and mixtures of such these carbohydrates. In some embodiments the carbohydrate is sucrose, lactose, raffinose or trehalose.

Skim milk may be present in any suitable concentration that provides for sufficient protection of cells or encapsulated cells during freezing. In illustrative embodiments skim milk may be present in a composition (freezing solution) of the invention in a concentration of about 1% (w/v) to about 10% (w/v). In this context, it is noted that skim milk (also known as skimmed milk) is used in its regular meaning to refer to the milk that is obtained when all the cream (also called milkfat) is removed from whole milk. Any skim milk/skimmed milk that is available can be used in a freezing solution/composition of the invention. Typically, skim milk powder is used for the preparation of the freezing composition of the invention. Thus, the concentration of the skim milk given herein is referred to as weight-% skim milk based on the volume of the freezing solution.

Also glycerol may be present in a composition of the invention in any suitable concentration that provides for sufficient protection of cells or encapsulated cells during freezing. In illustrative embodiments glycerol may be present in a freezing solution of the invention in a concentration of about 0.2 (w/v) to about 5% (w/v).

Also the carbohydrate may be present in a composition of the invention in any suitable concentration that provides for sufficient protection of cells or encapsulated cells during freezing. In illustrative embodiments the carbohydrate may be present in a freezing solution of the invention in a concentration of about 1% (w/v) to about 15% (w/v).

In illustrative embodiments of such a composition, skim milk is present in a concentration of about 3% (w/v) to about 8% (w/v), glycerol is present in a concentration of about 0.5% (w/v) to about 2% (w/v) and the carbohydrate is present in a concentration of about 5% (w/v) to about 13% (w/v). In one further illustrative embodiment, a freezing composition of the invention contains about 5% (w/v) skimmed milk, about 1% (w/v) glycerol and about 10% (w/v) of the carbohydrate. For the sake of illustration it is noted here that such a solution may be prepared by weighing out 1 g of glycerol, 5 g of skim milk powder and 10 g of trehalose into a 100 ml graduated measuring device. Then, the volume of the solution is made up to 100 ml with double distilled sterile water.

In line with the above disclosure, a composition of the invention that contains skim milk, glycerol and a carbohydrate can be used for the freezing of encapsulated cells as disclosed herein. However, such a composition of the invention that contains skim milk, glycerol and a carbohydrate can also be used for preparing encapsulated cells for freeze-drying, meaning in the consecutive incubation of encapsulated cells with increasing concentrations of cryoprotectant as disclosed herein. Accordingly, the invention is also directed to a method of preparing encapsulated cells for freeze-drying, wherein the method comprises incubating the encapsulated cells in a composition of the invention that contains skim milk, glycerol and a carbohydrate.

The invention will now be further illustrated by the following non-limiting experimental examples.

EXAMPLES

Example 1: Freeze Drying with Stepwise Addition of Cryoprotectant to the Incubation Solution Experimental Data:

Lactobacillus acidophilus probiotic bacteria were encapsulated, freeze-dried, rehydrated and tested for metabolic activity as a measure of viability. The capsules were analysed for structural integrity after freeze-drying and rehydration.

Bacterial Encapsulation

A bacteria culture of Lactobacillus acidophilus at an optical density of 1 OD at a wavelength of 600 nm was harvested and encapsulated in sodium cellulose sulphate and poly-diallyl dimethyl ammonium chloride (pDADMAC—also known under its International Nomenclature Cosmetic Ingredient (INCI) name Gel8). Encapsulated bacteria were cultured in de Man, Rogosa and Sharpe (MRS) medium at 37° C. with shaking at 50 rpm.

Freeze-Drying (Lyophilisation)

Encapsulated bacteria and free bacteria were frozen in an ethanol/dry ice bath using stepwise addition of 5% skim milk, 1% glycerol or DMSO in double distilled, sterile water as a cryoprotectant and then stored at −80° C. The freeze medium for the free bacteria is the same as for the encapsulated bacteria except that it is not added in a stepwise manner.

For the encapsulated bacterial cells, cryoprotectants were added in step-wise fashion as follows:

General Procedure (for "Serial Dilution" of the Culture Media):

Using a maximum of 1,000 capsules per ml of or any multiple thereof the capsules (containing the bacteria) were placed in a 50 ml falcon tube containing fresh MRS medium. To this cell suspension (incubation solution), 0.5 ml/ml of the freezing medium was added as cryoprotectant to yield a freezing medium with 50% concentration of the cryoprotectant (v/v). In illustrative terms, if the total volume of the cell suspension was 1 ml, then 0.5 ml medium were removed and 0.5 ml of freezing media was added to yield a 50% dilution of both). The encapsulated cells were incubated for 25 minutes and then further 50% (v/v) of the incubation solution was swapped for cryopreservation media (i.e. in case of a total volume of 1 ml, then 0.5 ml were removed and 0.5 ml of freezing media were added to yield a concentration of 75% (v/v) of the freezing media. The incubation was again carried out again for 25 minutes before in subsequent steps again 50% of the incubation media was replaced by freezing media. In the last incubation step, the medium on the capsules is 100% freezing medium.

(A) Step-Wise Addition of DMSO Cryoprotectant 16 capsules were placed in a 50 ml falcon tube containing 9 ml of fresh MRS medium. To this cell suspension (incubation solution), 200 µl of DMSO were added as cryoprotectant to yield an initial DMSO concentration of approximately 2% (v/v). The encapsulated cells were incubated for 25 minutes and then further 200 µl DMSO were added to yield a DMSO concentration of about 4.2% (v/v). The incubation was again carried out for 25 minutes before in 3 subsequent steps additional 200 µl DMSO were added to reach a final DMSO concentration of 10% (1 ml DMSO in 10 ml incubation solution).

(B) Step-Wise Addition of a Skim Milk/Glycerol Mixture as Cryoprotectant (5% Skim Milk and 1% Glycerol in Water)

In this example, 100 large hand made capsules were placed in a 50 ml falcon tube containing 9 ml of fresh MRS medium. 5 ml of the MRS medium were taken out from falcon tube and 5 ml of an incubation solution containing skim milk as cryoprotectant (5% skim milk (w/v) and 1% glycerol (w/v) in water) was added in the subsequent consecutive incubation steps. In this experiment six incubation steps were performed, in which the concentration of the cryoprotectant was increased in order of 50%, 75%, 87.5%, 93.75%, 97%, and 100%, meaning in the last incubation step the encapsulated cells are in the freezing media. The incubation period in each step after addition of the skim milk cryoprotectant was approximately 25 minutes. At the end of each incubation step the capsules settle down via gravity, thereby allowing the incubation medium to be removed via pipetting. After the last incubation step with 5% skim milk (w/v) and 1% glycerol (w/v) in water both frozen encapsulated bacteria and free bacteria were then directly subjected in this freezing solution (i.e. without any washing step) to lyophilisation overnight. For freeze-drying, firstly the capsules plus 100% freezing medium are shock-frozen using a 96% ethanol/dry ice bath. The shock-frozen pellet can then be stored at −80° C. or sent for freeze-drying immediately. Any freeze-drying machine can be used for the lyophilisation process by following the manufacturer's instructions. For the present experiments, the Thermo Scientific ModulyoD-230 device was used. The results of these experiments are shown in FIG. 1 to FIG. 9. As can be seen from the bright field microscopic images of capsules of FIG. 1, the consecutive incubation of the capsules in the method of the present invention provide, after re-hydration, an intact encapsulation and thus enhances the structural integrity of the encapsulation. See in this regard also the images shown in FIG. 4 and FIG. 5 that show that the cellulose sulphate capsules that were treated using an embodiment of the inventive method (using increasing concentrations of skim milk in the incubation steps) and then freeze-dried either in liquid nitrogen or an ethanol/dry ice maintain their original spherical shape with smooth surface after rehydration while, as evident from the images shown in FIGS. 6 to 9 capsules that were freeze-dried in various buffers without cryoprotectant are to a large extent damaged or destroyed.

Figure 2:
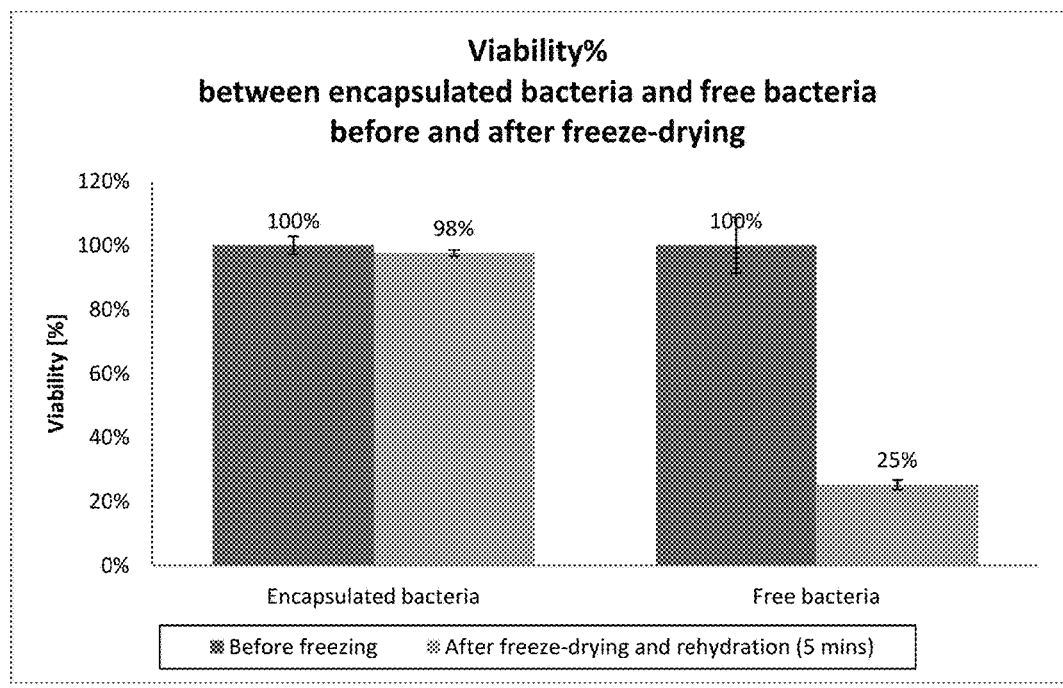
FIG. 2 shows the protective effect of capsules on *Lactobacillus acidophilus* bacteria during freeze-drying, using an incubation solution containing skim milk and glycerol (5% skim milk and 1% glycerol in water) as cryoprotectant. The protection effect was examined by a viability test following rehydration of the freeze-dried bacteria. The viability was compared to freshly encapsulated bacterial cells as reference and is expressed in % viability.

In addition to maintaining the structural integrity of the capsules with the cells contained therein, the freeze-drying method of the invention also provides for a significantly higher survival rate of the encapsulated cells. FIG. 2 shows the protective effect of the (intact) capsules on the tested bacteria during freeze-drying, when using, in preparation of the freezing, an incubation solution containing increasing amounts of skim milk and glycerol as cryoprotectant. The protective effect was examined by a viability test that was done one day after free-drying following rehydration of the freeze-dried bacteria. The viability was compared to freshly encapsulated bacterial cells as reference and is expressed in % viability. As illustrated in FIG. 2, after being subjected to the freeze-drying method of the invention capsules protect the bacteria from freeze drying (98% viability in encapsulated bacteria compared to 25% viability in free cells), meaning the viability of encapsulated bacteria is significantly higher than that of free bacteria.

Figure 3:
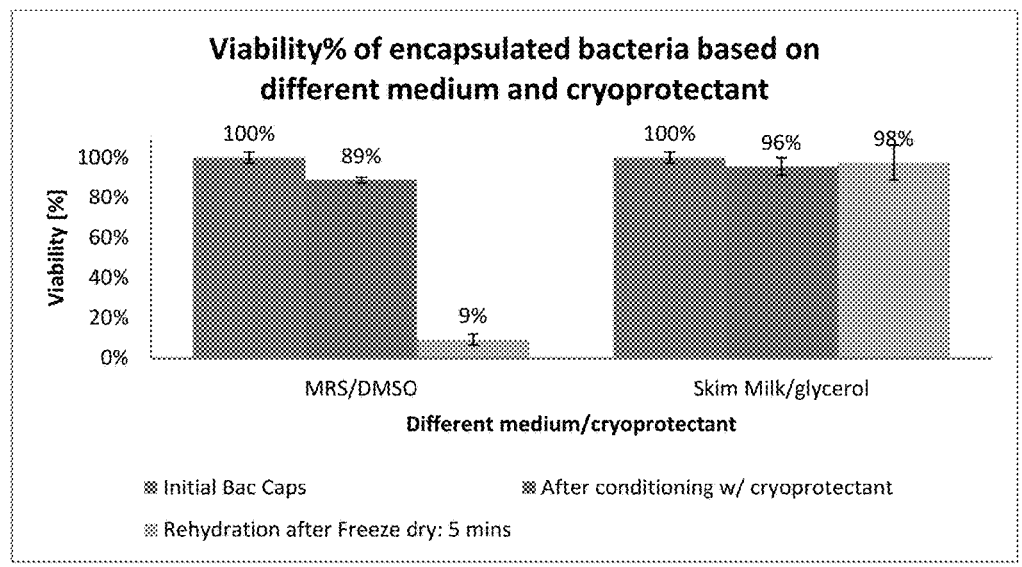
FIG. 3 shows the comparison of two different freeze media/incubation solutions (incubation solution 1: de Man, Rogosa and Sharpe (MRS) medium containing DMSO as cryoprotectant, incubation solution 2: 5% skim milk and 1% glycerol in water) with regard to survival of the *Lactobacillus acidophilus* bacteria during freeze-drying.
Figure 4:
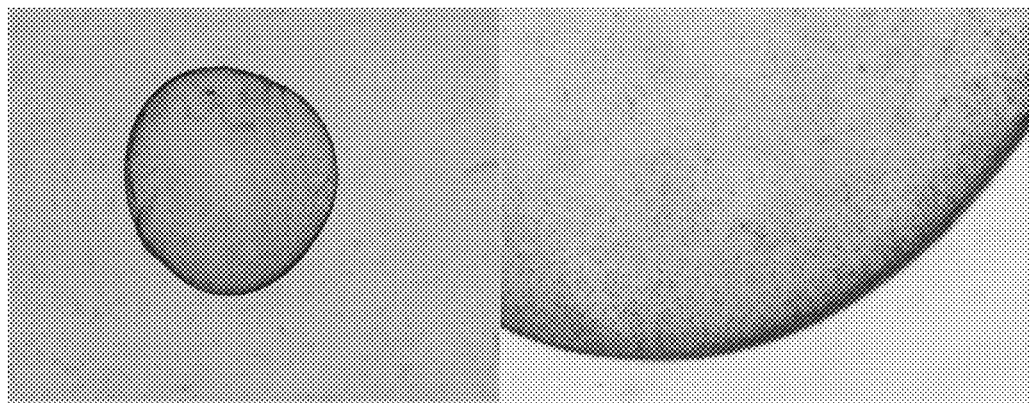
FIG. 4 shows bright field microscopic images of an empty capsule which has been re-hydrated after freeze-drying. The freezing medium used was skim milk with 1% glycerol. The freezing step prior to freeze-drying was carried out in liquid nitrogen.
Figure 5:
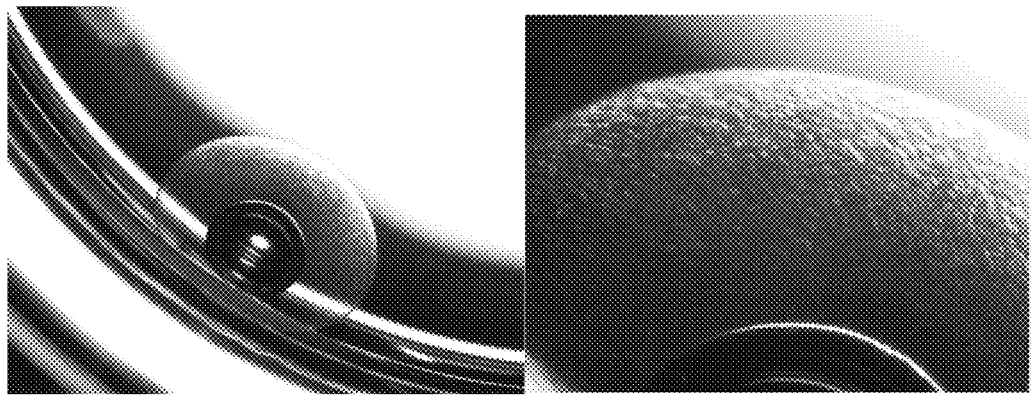
FIG. 5 shows bright field microscopic images of an empty capsule which has been re-hydrated after freeze-drying. The freezing medium used was skim milk with 1% glycerol. The freezing step prior to freeze-drying was carried out in an ethanol/dry ice bath.
Figure 6:
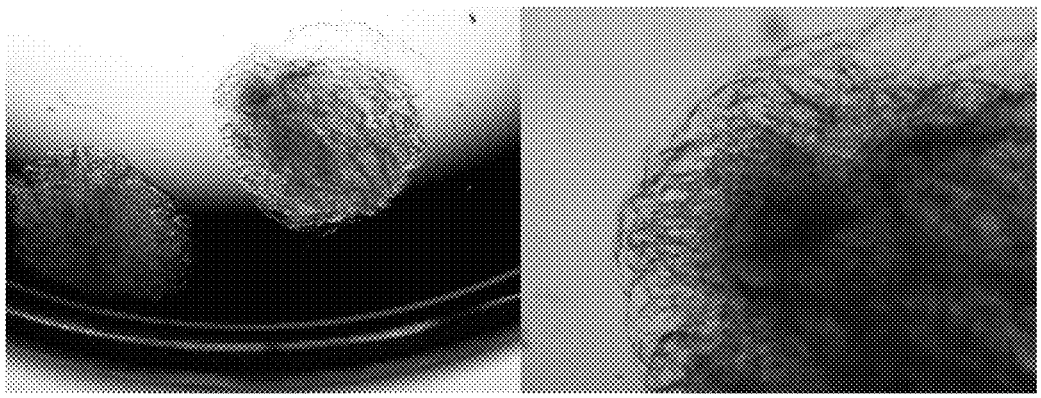
FIG. 6 shows bright field microscopic images of an empty capsule freeze-dried in phosphate buffered saline (PBS) without cryoprotectant with the pre-freezing step carried out in an ethanol/dry ice bath.
Figure 7:
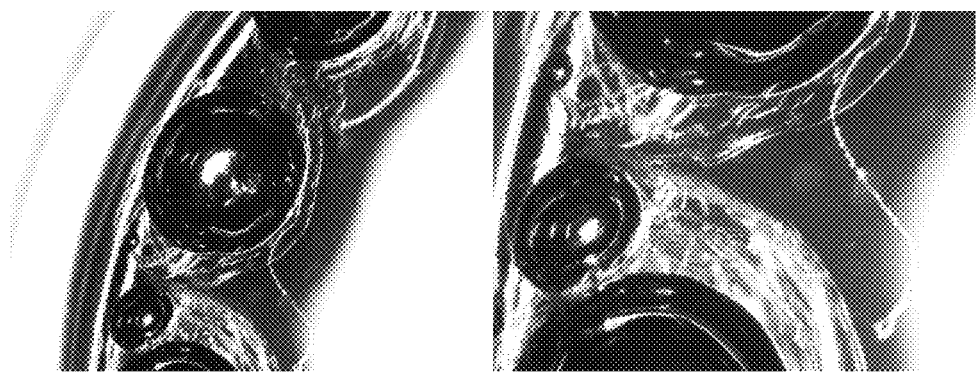
FIG. 7 shows bright field microscopic images of an empty capsule freeze-dried in PBS with 10% DMSO, with the pre-freezing step being carried out in an ethanol/dry ice bath.
Figure 8:
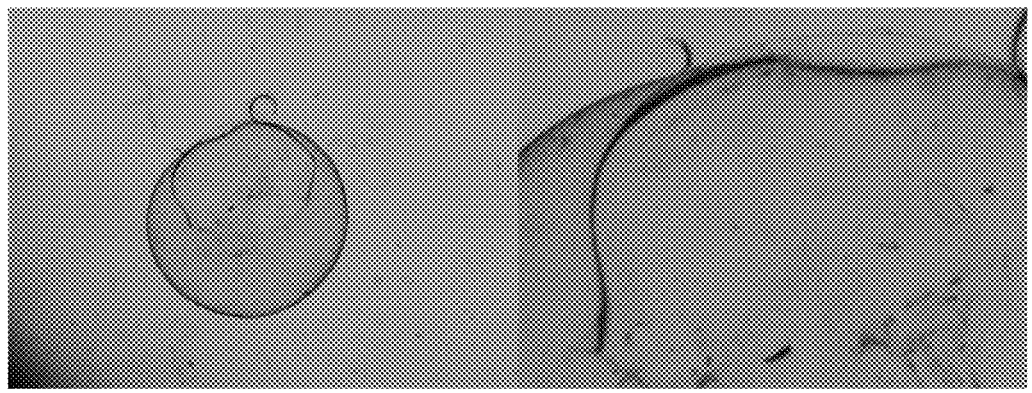
FIG. 8 shows bright field microscopic images of an empty capsule freeze-dried in MRS with no cryoprotectant, with the pre-freezing being carried out in liquid nitrogen.
Figure 9:
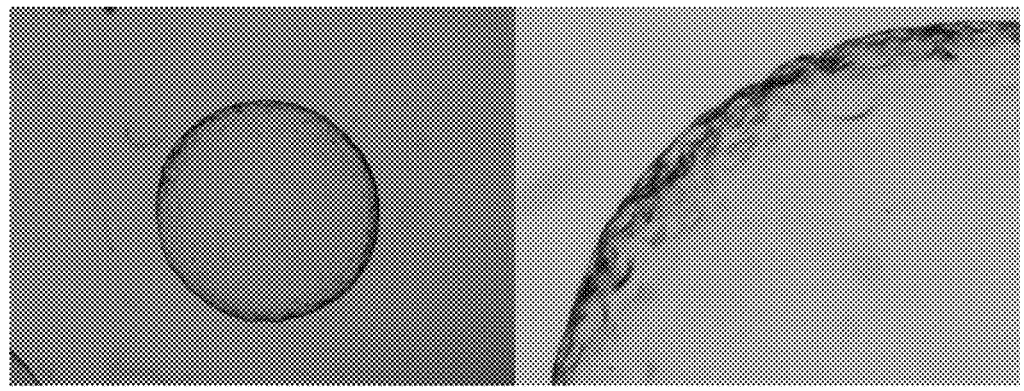
FIG. 9 shows bright field microscopic images of an empty capsule freeze-dried in MRS without cryoprotectant, with the freezing being carried out in an ethanol/dry ice bath.

FIG. 3 shows the comparison of the two different/incubation solutions used in the present example (incubation solution 1: MRS medium containing increasing amounts of DMSO as cryoprotectant, incubation solution 2 containing increasing amounts of skim milk with regard to survival of the bacteria during the freeze-drying. As depicted in FIG. 3, incubation with increasing concentration of skim milk (besides having glycerol an additional cryoprotectant) provides for unchanged survival rate compared to the freshly encapsulated bacterial cells that have not undergone freeze-drying, while the treatment of DMSO works but is less efficient with a survival rate of only 9%.

Example 2: Effect of Trehalose and Skim Milk as Cryoprotectant on the Survival of Sodium Cellulose Sulphate Encapsulated *Lactobacillus*

In this example, the survival of encapsulated *Lactobacillus acidophilus* freeze-dried was tested with or without 10% trehalose as a supplementary cryoprotectant when stored under ambient conditions. The freeze drying solution that was also used for the consecutive incubation step was an aqueous solution containing 5% skimmed milk (w/v), 1% glycerol (w/v), and 10% trehalose (w/v).

Experimental Details:

A previously frozen vial of the probiotic bacteria, *Lactobacillus acidophilus* was thawed out from −80° C. and 20 µl was added into 50 ml of MRS media. The bacteria were subsequently cultured overnight at 37° C. with a shaking speed of 50 rpm. The next day, the optical density of the bacterial culture was determined at 600 nm (OD600) on a Tecan Infinite M200. Typically an OD600 reading of 1 corresponds to when the bacteria are in the exponential growth phase. The bacteria should be in the exponential growth phase when encapsulated.

For the encapsulation of the bacteria, 100 ul of a bacterial culture with an OD600 reading of 1 was mixed with 2 ml 1.8% sodium cellulose sulphate containing 0.9% sodium chloride. A 5 ml syringe and a 23 G needle were used for the encapsulation process. The bacteria culture was mixed with the sodium cellulose sulphate and dropped into a gelation bath containing 150 ml of 1.3% pDADMAC (24 kDa), 0.9% sodium chloride. The capsules were allowed to gelate in the pDADMAC for 4 mins. Subsequently, 300 ml of 1× Phosphate Buffered Saline (PBS) was added and the capsules washed for 8 mins. 300 ml of the washing solution was then removed and a further 400 ml of PBS was added and the capsules washed for an additional 4 mins. The washing solution was then drained and a further 3×100 ml washes with PBS then 3×30 ml washes with fresh MRS were performed. The capsules were then transferred to a 250 ml conical flask with 100 ml of fresh MRS media. These capsules were cultured overnight at 37° C. with a shaking speed of 50 rpm.

For the free bacteria, 5 ml of the overnight culture of Lactobacillus cells at OD600=1 was transferred into a 15 ml falcon tube and centrifuged at 3000 g for 5 mins. The bacterial pellet was resuspended in 5 ml cryopreservation medium (5% skim milk (w/v), 1% glycerol (w/v) in water) with or without 10% (w/v) trehalose. The resuspended bacteria were then aliquotted into 10×0.5 ml portions in 15 ml falcon tubes. 5 ul of the resuspended cells were placed into each of 4 wells of a 96 well plate and an Alamar Blue assay was carried out to determine the metabolic activity of the bacterial cells. Alamar Blue® is a proven cell viability indicator that uses the natural reducing power of living cells to convert resazurin to the fluorescent molecule, resorufin. Resazurin, a non-fluorescent indicator dye, is converted to bright red-fluorescent resorufin via the reduction reactions of metabolically active cells. The amount of fluorescence produced is proportional to the number of living cells. 100 ul of fresh MRS media and 10 ul of the Alamar Blue reagent were added to the 5 ul bacterial sample and the samples incubated at 37° C. with a shaking speed of 50 rpm for 1 hr. The Alamar Blue assay plate was read on a Tecan Infinite M200. The rest of the free bacteria cells in the cryoprotective media are frozen in ethanol/dry ice bath and then stored at −80° C.

After overnight culture the bacteria containing capsules were washed with 3×50 ml fresh MRS media in the 250 ml flask first and then placed in 15 ml falcon tube with 10 ml of fresh MRS media. 5 ml of MRS media was taken out and 5 ml of cryopreservation medium (as for free bacteria) with or without 10% (w/v) trehalose was added. The capsules were incubated in this suspension for 25 minutes then 5 ml of the medium removed and replaced with 5 ml of fresh cryopreservation medium (with or without 10% trehalose as appropriate). This procedure was repeated an additional 4 times, thus raising the proportion of cryopreservation medium from 50% after the first addition of cryopreservation medium to 98.5% finally. Subsequently, 1 capsule from the medium was placed into each of 4 wells of a 96 well plate and an Alamar Blue assay was carried out to determine the level of metabolic activity of the bacterial cells in the capsules. 10 ul of Alamar Blue reagent and 100 ul of fresh MRS medium was added to each well containing the capsules and the samples incubated at 37° C. with a shaking speed of 50 rpm for 1 hr. The Alamar Blue assay plate was read on a Tecan Infinite M200. 4 capsules from the cryopreservation medium were placed into 15 ml falcon tubes with 500 ul of aqueous freeze drying solution containing 5% skim milk, 1% with or without 10% trehalose (as appropriate). These capsules were then frozen in an ethanol/dry ice bath and then stored at −80° C.

The falcon tubes containing either the free bacteria or capsules with the skim milk cryoprotectant with or without 10% trehalose were freeze-dried overnight using a Thermo-Scientific Modulyo D-230 freeze-drier. To test the survival of the freeze-dried bacteria, at each point of time duplicate samples of freeze-dried free Lactobacillus and encapsulated Lactobacillus were rehydrated using 500 ul of Millipore water, or 5-10 ml of MRS media respectively, for 5 mins. An Alamar Blue assay was then performed on both the free Lactobacillus and Lactobacillus capsules. The assay consisted of quadruplicate replicates of each of the following conditions for each of the duplicate samples:
1. Blank samples (100 ul MRS media+10 ul alamar blue)
2. Free Lactobacillus samples freeze-dried with trehalose (5 ul of rehydrated culture+100 ul MRS media+10 ul Alamar Blue)
3. Free Lactobacillus samples freeze-dried without trehalose (5 ul of rehydrated culture+100 ul MRS media+10 ul Alamar Blue)
4. Encapsulated bacteria samples freeze dried with trehalose (1 capsule per well+100 ul MRS media+10 ul alamar blue)
5. Encapsulated bacteria samples freeze dried without trehalose (1 capsule per well+100 ul MRS media+10 ul alamar blue)

The samples were incubated at 37° C. with a shaking speed of 50 rpm for 1 hr. The Alamar Blue assay plate was read on a Tecan Infinite M200. The points of time at which the samples were rehydrated were at weeks 1, 2, 3, 4, 6, 7 and 8 post freeze-drying to assess the viability of bacteria after cryopreservation with 5% skim milk, 1% glycerol and with or without 10% trehalose at room temperature over a period of 2 months after freeze-drying.

Figure 10:
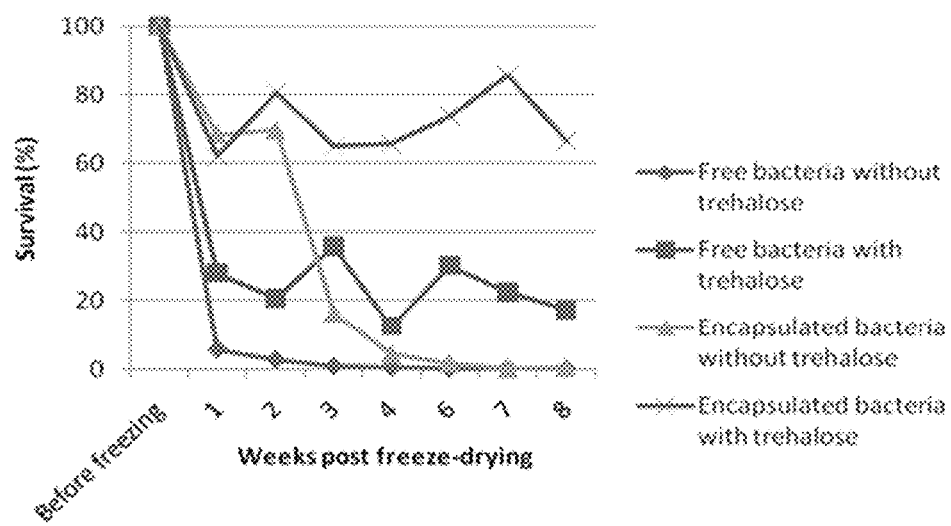
FIG. 10 shows the results of an embodiment of the freezing-drying method of the invention using a combination of 5% skimmed milk, 1% glycerol and 10% trehalose as cryo-protectant both as incubation solution for the sequential incubation with increasing concentrations of the cryoprotectant and as freeze-drying solution. The following samples were employed in this experiment: 1) Free (not encapsulated) *Lactobacillus* samples freeze-dried with skim milk/glycerol/trehalose (filled rhombes), 2) free *Lactobacillus* samples freeze-dried without skim milk/glycerol/trehalose (filed squares), 3) encapsulated *Lactobacillus* bacteria samples freeze dried using the method of the invention with concentration of skim milk, glycerol and trehalose as cryoprotectant in the incubation solution (crosses) (the increasing concentrations of the cryoprotectant were achieved by serially diluting in each incubation step the bacterial growth solution from 100% to 50% to 25% to 12.5% to 6.25% to 3.125% to 0% with cyroprotectant solution (5% skim milk powder, 1% glycerol and 10% trehalose), 4) encapsulated *lactobacillus* bacteria samples freeze dried without trehalose (filled triangles). The time points at which the samples were rehydrated were 1, 2, 3, 4, 6, 7 and 8 weeks post freeze-drying to assess the viability of bacteria after cryopreservation with or without trehalose at room temperature over a period of 2 months after freeze-drying. Each data point in FIG. 10 represents the average of duplicate freeze-dried samples (each sample tested in quadruplicate) with two exceptions: free bacteria with 10% trehalose at week 6 and encapsulated bacteria with 10% trehalose at week 8. RFU=Relative fluorescent units.

The results of this experiment are shown in FIG. 10. Each data point in FIG. 10 represents the average of duplicate freeze-dried samples (each sample tested in quadruplicate) with two exceptions: free bacteria with 10% trehalose at week 6 and encapsulated bacteria with 10% trehalose at week 8 where, in both cases, one sample of the duplicate was completely degraded (the reason for which is unclear) and has not been included. The survival rate was determined in relative fluorescent units (RFU). As can be seen from FIG. 10, the inventive freeze-drying method in which the encapsulated bacterial cells are consecutively incubated in a solution that contains increasing concentrations of the freezing medium (containing 5% skimmed milk, 1% glycerol, 10% trehalose) as cryoprotectant provides a survival rate of more than 60% of the cells and thus a significant improvement to the survival rate of the free cells. While this survival rate of more than 60% was achieved for a storage period of two weeks for treatment of the cells with increasing concentrations of skim milk only, the addition of trehalose in a concentration of 10% (w/v) achieved to maintain this significantly increased survival rate for the entire test period of 8 weeks, meaning to extend the shelf-life of the capsules/ encapsulated cells. This results also shows that the method of the invention and the freeze-dried encapsulated cells that can be obtained by this method have promising prospects for commercial applications for cells such as probiotic cells (but also other cells) for which the cells are stored for a certain period of time till used.

Example 3: Freeze-Drying of Encapsulated *Lactobacillus casei* Using a Composition Comprising Skim Milk, Trehalose and Glycerol as Cryoprotectant A previously frozen vial of the probiotic bacteria, *Lactobacillus casei* was thawed out from −80° C. and 20 µl was added into 50 ml of MRS media. The bacteria were subsequently cultured overnight at 37° C. with a shaking speed of 50 rpm. The next day, the optical density of the bacterial culture was determined at 600 nm (OD600) on a Tecan Infinite M200. Typically an OD600 reading of 1 corresponds to when the bacteria are in the exponential growth phase. The bacteria should be in the exponential growth phase when encapsulated.

For the encapsulation of the bacteria, 100 ul of a bacterial culture with an OD600 reading of 1 was mixed with 2 ml 1.8% sodium cellulose sulphate containing 0.9% sodium chloride. A 5 ml syringe and a 23 G needle were used for the encapsulation process. The bacteria culture was mixed with the sodium cellulose sulphate and dropped into a gelation bath containing 150 ml of 1.3% pDADMAC (24 kDa), 0.9% sodium chloride. The capsules were allowed to gelate in the pDADMAC for 4 mins. Subsequently, 300 ml of 1× Phosphate Buffered Saline (PBS) was added and the capsules washed for 8 mins. 300 ml of the washing solution was then removed and a further 400 ml of PBS was added and the capsules washed for an additional 4 mins. The washing solution was then drained and a further 3×100 ml washes with PBS then 3×30 ml washes with fresh MRS were performed. The capsules were then transferred to a 250 ml conical flask with 100 ml of fresh MRS media. These capsules were cultured overnight at 37° C. with a shaking speed of 50 rpm.

After the overnight culture the bacteria containing capsules were washed with 3×50 ml fresh MRS media in the 250 ml flask first and then placed in 15 ml falcon tube with 10 ml of fresh MRS media. 5 ml of MRS media was taken out and 5 ml of cryopreservation medium with (5% skim milk (w/v), 1% glycerol (w/v), 10% (w/v) trehalose in water) was added. The capsules were incubated in this suspension for 25 minutes then 5 ml of the medium removed and replaced with 5 ml of fresh cryopreservation medium. This procedure was repeated an additional 4 times, thus raising the proportion of cryopreservation medium from 50% after the first addition of cryopreservation medium to 98.5% finally.

Finally, capsules from the cryopreservation medium were placed into 15 ml falcon tubes with 500 ul of aqueous freeze drying solution containing 5% skim milk, 1% glycerol and 10% trehalose. These capsules were then frozen in an ethanol/dry ice bath and then stored at −80° C.

Figure 11A:
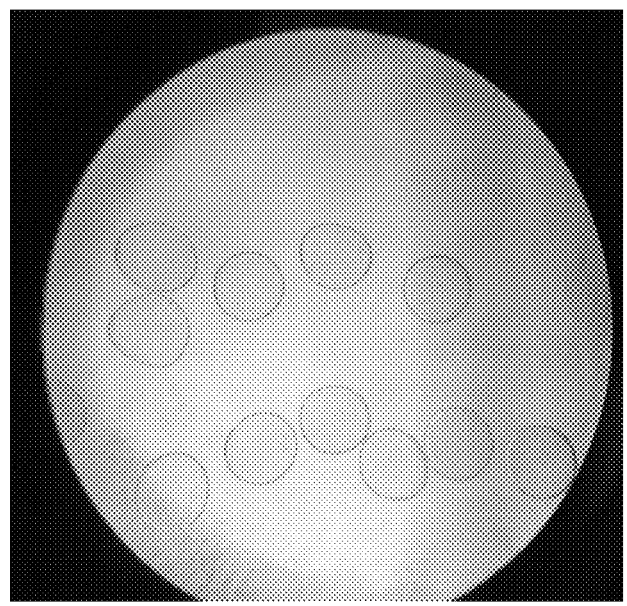
FIG. 11 shows *Lactobacillus casei* capsules at different points after encapsulation and freeze-drying, with FIG. 11A showing *Lactobacillus casei* capsules immediate after encapsulation, FIG. 11B showing *Lactobacillus casei* capsules one day after encapsulation before freeze-drying, and FIG. 11C showing rehydrated freeze-dried *Lactobacillus casei* capsules.
Figure 11B:
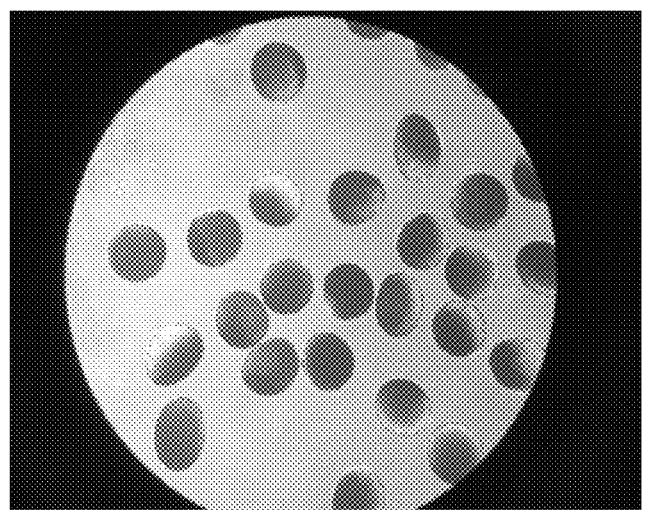
Figure 11C:
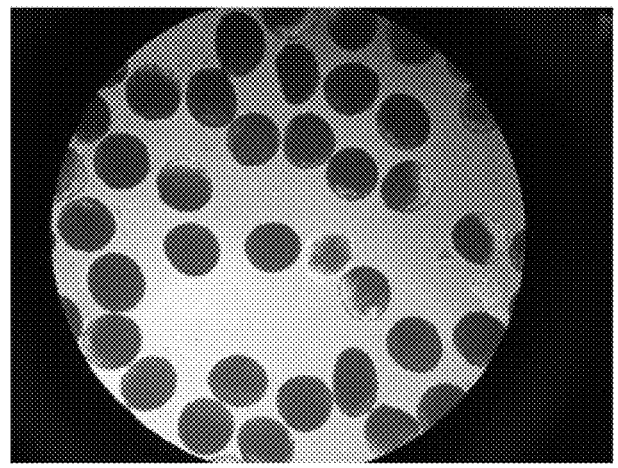

As can be seen from FIG. 11A to 11C which show the encapsulated cells before and after encapsulation (FIG. 11A shows *Lactobacillus casei* capsules immediate after encapsulation, FIG. 11B shows *Lactobacillus casei* capsules one day after encapsulation before freeze-drying, and FIG. 11C shows rehydrated freeze-dried *Lactobacillus casei* capsules), the *Lactobacillus casei* capsules appeared be intact after the freeze-drying, meaning not affected by the freeze-drying.

Figure 12:
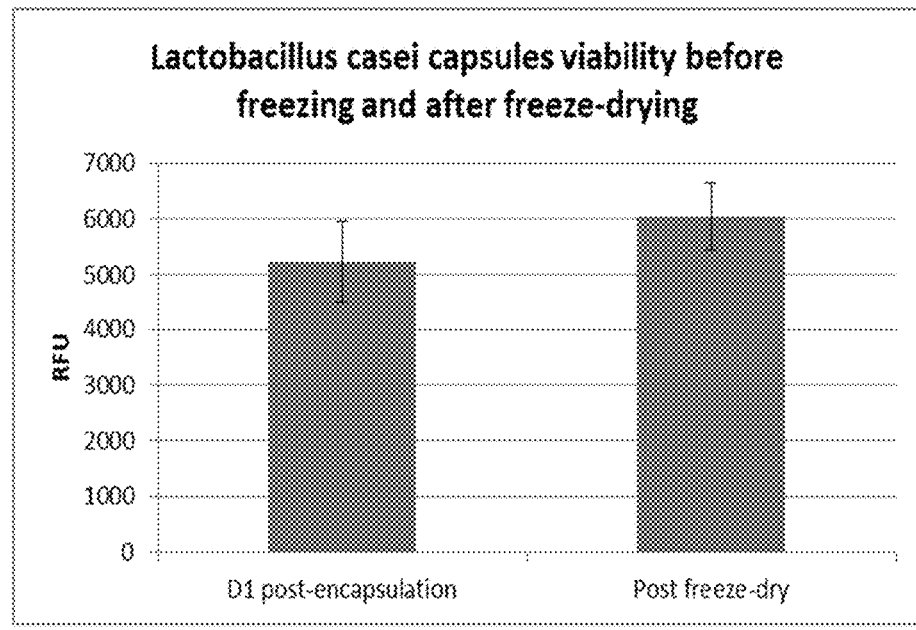
FIG. 12 shows the viability comparison of *Lactobacillus casei* capsules one day before and after freeze-drying.

In addition to visual examination, the viability of encapsulated *Lactobacillus casei* bacteria was checked before freeze drying and after freeze drying as explained above in Example 2. As can be seen from FIG. 12, the result thereof shows the viability of the *Lactobacillus casei* bacteria was affected by the freeze-drying, meaning full viability was picked up after freeze-drying. Thus, Example 3 confirms the effectiveness and suitability of the freeze-drying method and respective composition of the present invention.

Example 4: Freeze-Drying of Encapsulated *Bifidobacterium infantis longum* using a Composition Comprising Skim Milk, Trehalose and Glycerol as Cryoprotectant

*Bifidobacterium infantis longum* are an example of strict anaerobic bacteria. The cells were therefore cultured under anaerobic conditions in MRS medium, at 37° C. and 50 rpm for overnight. Gaspak (BD) was used to created strict anaerobic environment during culturing.

After cultivation *Bifidobacteria* were encapsulated using sodium cellulose sulphate as described in Example 2 and 3, however under anaerobic conditions. After the overnight culture the bacteria containing capsules were washed with 3×50 ml fresh MRS media in the 250 ml flask first and then placed in 15 ml falcon tube with 10 ml of fresh MRS media. 5 ml of MRS media was taken out and 5 ml of cryopreservation medium with (5% skim milk (w/v), 1% glycerol (w/v), 10% (w/v) trehalose in water) was added. The capsules were incubated in this suspension for 25 minutes then 5 ml of the medium removed and replaced with 5 ml of fresh cryopreservation medium. This procedure was repeated an additional 4 times, thus raising the proportion of cryopreservation medium from 50% after the first addition of cryopreservation medium to 98.5% finally.

Finally, capsules from the cryopreservation medium were placed into 15 ml falcon tubes with 500 ul of aqueous freeze drying solution containing 5% skim milk, 1% glycerol and 10% trehalose. These capsules were then frozen in an ethanol/dry ice bath and then stored at −80° C.

Figure 13A:
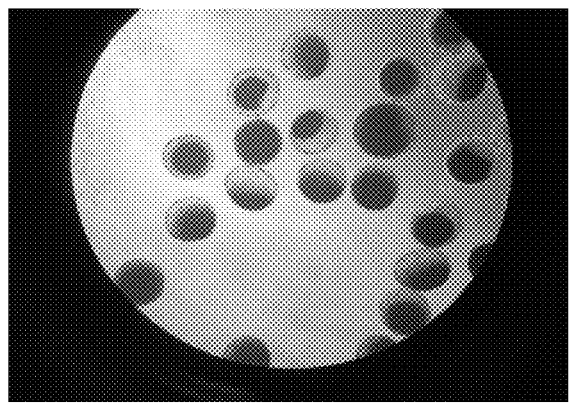
FIG. 13 shows *Bifidobacterium infantis longum* capsules at different points after encapsulation and freeze-drying, with FIG. 13A showing *Bifidobacterium infantis* capsules one day after encapsulation before freeze-drying, and FIG. 13B showing rehydrated freeze-dried *Bifidobacterium infantis longum* capsules.
Figure 13B:
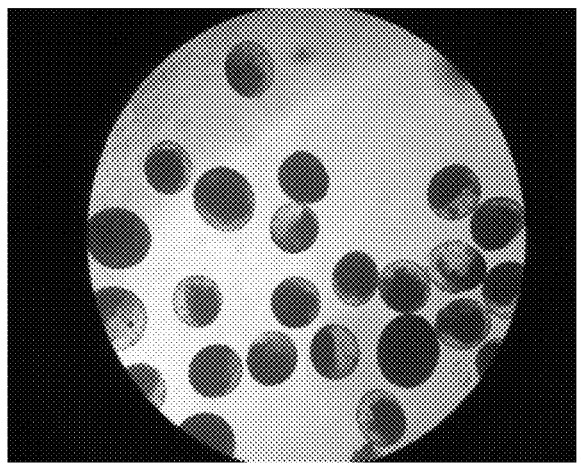

As can be seen from FIG. 13 which shows the encapsulated cells before and after encapsulation (FIG. 13A shows capsules one day after encapsulation before freeze-drying, and FIG. 13B shows rehydrated freeze-dried *Bifidobacterium infantis longum* capsules), the *Bifidobacterium infantis longum* capsules appeared be slightly less intact after the freeze-drying.

Figure 14:
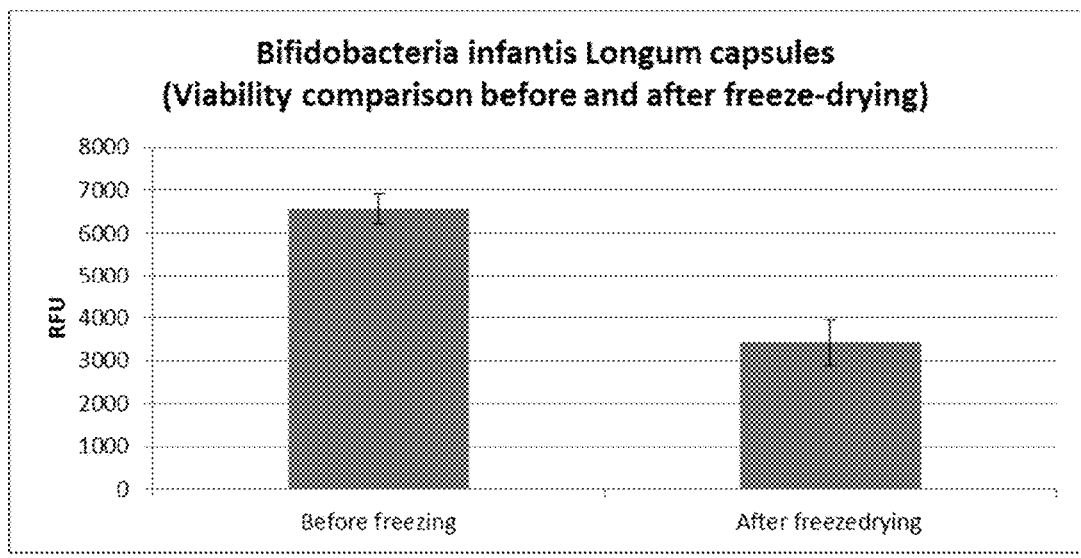
FIG. 14 shows the viability comparison of *Bifidobacterium infantis longum* capsules one day before and after freeze drying.

In addition to visual examination, the viability of the encapsulated *Bifidobacterium infantis* bacteria was checked before freeze drying and after freeze drying as explained above in Example 2. As can be seen from FIG. 14, the viability of *Bifidobacterium infantis longum* was somehow affected by the freeze-drying, as FIG. 14 shows that about 50% of bacteria were viable after freeze-drying. However, it is believed that the viability of free (not encapsulated) *Bifidobacterium infantis* bacteria will be much lower. In addition, higher viability can be expected by the capsules are perfectly dried during freeze-drying process. Thus, also Example 4 confirms the effectiveness and suitability of the freeze-drying method and a respective composition of the present invention.

The invention illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of preparing encapsulated cells for freeze-drying, the method comprising at least two consecutive incubation steps, wherein the encapsulated cells are incubated in each incubation step in an incubation solution containing cryoprotectant over a suitable period of time, wherein the concentration of cryoprotectant in the incubation solution is increased with each subsequent incubation step, wherein the encapsulated cells are bacterial cells or yeast cells, and wherein the cryoprotectant is a composition comprising skim milk, glycerol and trehalose, wherein in the composition skim milk is present in a concentration of 3% (w/v) to 8% (w/v), glycerol is present in a concentration of 0.5% (w/v) to 2% (w/v) and trehalose is present in a concentration of 5% (w/v) to 13% (w/v).

2. The method of claim 1, comprising 3, 4, 5, 6, 7, 8, 9 or 10 incubation steps wherein in each incubation step the concentration of the cryoprotectant is increased.

3. The method of claim 1, wherein the cells are probiotic cells.

4. The method of claim 3, wherein the probiotic cells are selected from the group consisting of *Saccharomyces cereviseae, Bacillus coagulans, Bacillus licheniformis, Bacillus subtilis, Bifidobacterium angulatum, Bifidobacterium animalis, Bifidobacterium bifidum, Bifidobacterium breve, Bifidobacterium infantis, Bifidobacterium lactis, Bifidobacterium longum, Enterococcus faecium, Enterococcus faecalis, Lactobacillus acidophilus, Lactobacillus amylovorus, Lactobacillus alimentarius, Lactobacillus bulgaricus, Lactobacillus casei* subsp. *casei, Lactobacillus casei* Shirota, *Lactobacillus curvatus, Lactobacillus delbrueckii* subsp. *lactis, Lactobacillus fermentum, Lactobacillus farciminus, Lactobacillus gasseri, Lactobacillus helveticus, Lactobacillus johnsonii, Lactobacillus lacti, Lactobacillus paracasei, Lactobacillus pentosaceus, Lactobacillus plantarum, Lactobacillus reuteri, Lactobacillus rhamnosus* (*Lactobacillus* GG), *Lactobacillus sake, Lactobacillus salivarius, Lactococcus lactis, Lactobacillus thermotolerans, Lactobacillus mucosae, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus,* and *Staphylococcus xylosus.*

5. The method of claim 1, further comprising freeze-drying the encapsulated cells.

6. The method of claim 2, further comprising freeze-drying the encapsulated cells.

7. The method of claim 3, further comprising freeze-drying the encapsulated cells.

8. The method of claim 4, further comprising freeze-drying the encapsulated cells.

* * * * *